US012620135B2

(12) United States Patent
Fang et al.

(10) Patent No.: US 12,620,135 B2
(45) Date of Patent: *May 5, 2026

(54) ENDOSCOPE DEVICE, ENDOSCOPIC MEDICAL ASSISTANCE SYSTEM AND ENDOSCOPIC IMAGE PROCESSING METHOD

(71) Applicant: Morning dew Creative Technical Co., Ltd., Taoyuan (TW)

(72) Inventors: Yuan-Ting Fang, Taoyuan (TW); Ming-Huang Hsiao, Taoyuan (TW)

(73) Assignee: Morning dew Creative Technical Co., Ltd., Taoyuan City (TW)

( * ) Notice: Subject to any disclaimer, the term of this patent is extended or adjusted under 35 U.S.C. 154(b) by 395 days.

This patent is subject to a terminal disclaimer.

(21) Appl. No.: 18/324,991

(22) Filed: May 28, 2023

(65) Prior Publication Data

US 2024/0331200 A1     Oct. 3, 2024

(30) Foreign Application Priority Data

Mar. 31, 2023    (TW) ................................. 112112441

(51) Int. Cl.
    *G06T 7/90*        (2017.01)
    *A61B 1/00*        (2006.01)
         (Continued)

(52) U.S. Cl.
    CPC ............ *G06T 7/90* (2017.01); *A61B 1/00009* (2013.01); *A61B 1/0638* (2013.01); *H04N 23/84* (2023.01);
         (Continued)

(58) Field of Classification Search
    CPC . G06T 2207/10024; G06T 2207/10028; G06T 2207/20221; G06T 5/50;
         (Continued)

(56) References Cited

U.S. PATENT DOCUMENTS 9,905,196 B2 *   2/2018   Pajak ..................... G09G 5/026
9,948,869 B2 *   4/2018   Fang .................... H04N 13/111
         (Continued)

FOREIGN PATENT DOCUMENTS

CN       102397049 A    4/2012
CN       102429624 A    5/2012
         (Continued)

*Primary Examiner* — Antoinette T Spinks
(74) *Attorney, Agent, or Firm* — Li & Cai Intellectual Property Office

(57) ABSTRACT

An endoscope device, an endoscopic medical assistance system and an endoscopic image processing method are provided. An endoscope in the endoscope device and the endoscopic medical assistance system senses light beams reflected by an object to generate initial images. After the initial images are aligned with each other to form a superimposed image, an image fusion device of the endoscopic medical assistance system analyzes features of the superimposed image to convert the superimposed image into a feature image. The image fusion device adjusts a color depth of each of a plurality of pixel points of the feature image according to a relationship between the color depth of each of the pixel points and a maximum color depth that are classified in the same color tone in each of pixel regions of the feature image. The image fusion device generates a fusion image according to the adjusted feature image.

8 Claims, 10 Drawing Sheets

(51) Int. Cl.
    *A61B 1/06*       (2006.01)
    *H04N 23/84*     (2023.01)

(52) U.S. Cl.
    CPC ............... *G06T 2207/10024* (2013.01); *G06T 2207/10068* (2013.01); *G06T 2207/20221* (2013.01)

(58) Field of Classification Search
    CPC .. G06T 7/50; G06T 7/90; G06V 10/44; G06V 10/56; G06V 10/764
    See application file for complete search history.

(56)            References Cited

U.S. PATENT DOCUMENTS 11,294,166 B2     4/2022   Duckett, II
    12,444,024 B2 *  10/2025  Wu ........................... G06T 7/90

| | | | |
|---|---|---|---|
| 2010/0014781 A1 * | 1/2010 | Liu | H04N 13/128 382/285 |
| 2012/0035419 A1 | 2/2012 | Ashida et al. | |
| 2012/0075449 A1 | 3/2012 | Yasuda | |
| 2015/0312451 A1 | 10/2015 | Lei | |
| 2018/0007285 A1 * | 1/2018 | Fang | H04N 13/00 |
| 2022/0026725 A1 | 1/2022 | Duckett et al. | |
| 2023/0064963 A1 * | 3/2023 | Shang | G06V 20/64 |
| 2023/0252637 A1 * | 8/2023 | Xu | G06V 10/771 382/173 |
| 2024/0331097 A1 * | 10/2024 | Wu | G06T 5/50 |

FOREIGN PATENT DOCUMENTS

| | | |
|---|---|---|
| TW | 201541959 A | 11/2015 |
| TW | 202122030 A | 6/2021 |
| TW | 202215370 A | 4/2022 |
| WO | WO2022036302 A1 | 2/2022 |

* cited by examiner

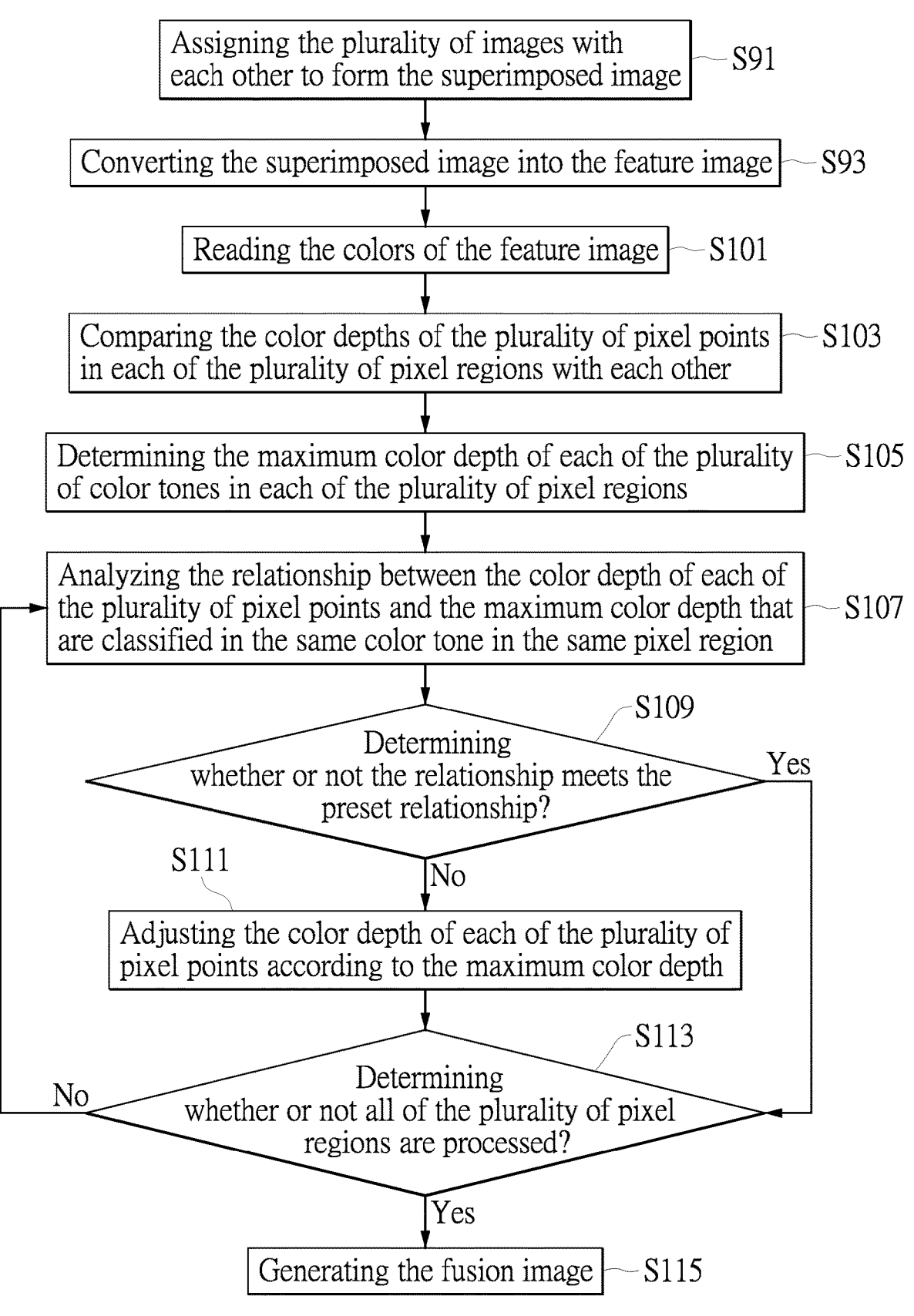

Assigning the plurality of images with each other to form the superimposed image ~S91

Converting the superimposed image into the feature image ~S93

Reading the colors of the feature image ~S101

Comparing the color depths of the plurality of pixel points in each of the plurality of pixel regions with each other ~S103

Determining the maximum color depth of each of the plurality of color tones in each of the plurality of pixel regions ~S105

Analyzing the relationship between the color depth of each of the plurality of pixel points and the maximum color depth that are classified in the same color tone in the same pixel region ~S107

Determining whether or not the relationship meets the preset relationship? ~S109   Yes No

S111

Adjusting the color depth of each of the plurality of pixel points according to the maximum color depth Determining whether or not all of the plurality of pixel regions are processed? ~S113   No Yes Generating the fusion image ~S115

FIG. 6

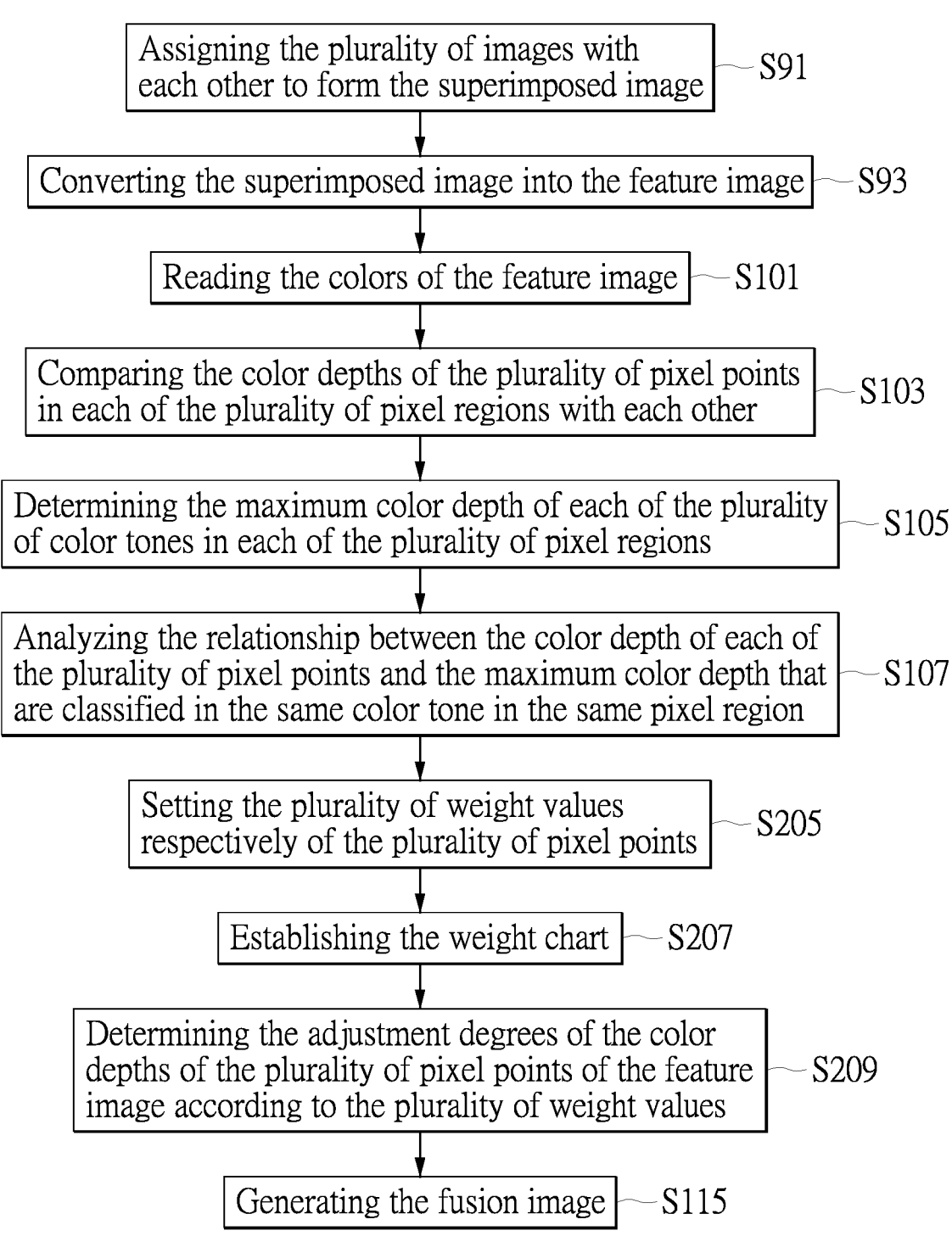

Assigning the plurality of images with each other to form the superimposed image — S91

Converting the superimposed image into the feature image — S93

Reading the colors of the feature image — S101

Comparing the color depths of the plurality of pixel points in each of the plurality of pixel regions with each other — S103

Determining the maximum color depth of each of the plurality of color tones in each of the plurality of pixel regions — S105

Analyzing the relationship between the color depth of each of the plurality of pixel points and the maximum color depth that are classified in the same color tone in the same pixel region — S107

Setting the plurality of weight values respectively of the plurality of pixel points — S205

Establishing the weight chart — S207

Determining the adjustment degrees of the color depths of the plurality of pixel points of the feature image according to the plurality of weight values — S209

Generating the fusion image — S115

FIG. 7

ENDOSCOPE DEVICE, ENDOSCOPIC MEDICAL ASSISTANCE SYSTEM AND ENDOSCOPIC IMAGE PROCESSING METHOD

CROSS-REFERENCE TO RELATED PATENT APPLICATION

This application claims the benefit of priority to Taiwan Patent Application No. 112112441, filed on Mar. 31, 2023. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an endoscope device, and more particularly to an endoscope device, an endoscopic medical assistance system and an endoscopic image processing method.

BACKGROUND OF THE DISCLOSURE

In recent years, medical capsules, such as capsule endoscopes, have been widely used in the medical field. After the medical capsule is swallowed into a human body, the medical capsule sequentially flows through a plurality of body parts inside the human body. At the same time, the medical capsule captures a plurality of images inside the plurality of body parts (such as organs, tissues and so on) of the human body.

However, the medical capsules such as the capsule endoscopes cannot capture the plurality of images of the same one of the body parts of the human body respectively under different colored lights inside the body parts of the human body. Furthermore, the images captured by the medical capsules such as the capsule endoscopes are blurred images. However, medical personnel must accurately diagnose health of the human body based on a clear image. Therefore, the plurality of images captured by the medical capsules must be further fused to form the clear image by a system for a long period of time. The medical personnel cannot instantly obtain the clear image for accurate diagnosis of the human health.

SUMMARY OF THE DISCLOSURE

In response to the above-referenced technical inadequacies, the present disclosure provides an endoscope device. After a plurality of ambient lights are irradiated on an object and then are reflected by the object to form a plurality of test lights, the endoscope senses parts of a plurality of colored light beams of the plurality of test lights that fall within a same one of a plurality of imaging ranges to generate each of a plurality of initial images, so as to generate the plurality of initial images respectively within the plurality of imaging ranges.

In certain embodiments, the endoscope includes a beam splitter and a plurality of image sensors. The beam splitter is configured to split each of the plurality of test lights into some of the plurality of colored light beams. The beam splitter is configured to reflect the plurality of colored light beams of the plurality of test lights respectively along a plurality of light reflecting paths. The plurality of image sensors disposed respectively within the plurality of imaging ranges. Each of the plurality of image sensors is disposed in a number of the plurality of light reflecting paths. The plurality of image sensors sense the plurality of colored light beams in the plurality of light reflecting paths to respectively generate the plurality of initial images within the plurality of imaging ranges.

In addition, the present disclosure provides an endoscopic medical assistance system. The endoscopic medical assistance system includes an endoscope and the image fusion device. After a plurality of ambient lights are irradiated on an object and then are reflected by the object to form a plurality of test lights, the endoscope senses parts of a plurality of colored light beams of the plurality of test lights that fall within a same one of a plurality of imaging ranges to generate each of a plurality of initial images, so as to generate the plurality of initial images respectively within the plurality of imaging ranges. The image fusion device is connected to the endoscope. The image fusion device aligns the plurality of initial images with each other to form a superimposed image. The image fusion device analyzes a plurality of features of the superimposed image and accordingly converts the superimposed image into a feature image. The image fusion device reads and identifies colors of a plurality of pixel points in a plurality of pixel regions of the feature image. The image fusion device compares color depths of the plurality of pixel points in each of the plurality of pixel regions of the feature image with each other. The image fusion device determines a largest one of the color depths of the plurality of pixel points that are classified in a same one of a plurality of color tones in each of the plurality of pixel regions as a maximum color depth of the same one of the plurality of color tones in each of the plurality of pixel regions of the feature image. The image fusion device analyzes a relationship between the color depth of each of the plurality of pixel points and the maximum color depth that are classified in the same one of the plurality of color tones in each of the plurality of pixel regions of the feature image. The image fusion device adjusts the color depth of each of the plurality of pixel points of the feature image according to the relationship between the color depth of each of the plurality of pixel points and the maximum color depth that are classified in the same one of the plurality of color tones in each of the plurality of pixel regions of the feature image. The image fusion device generates a fusion image according to the feature image on which the color depths of all of the plurality of pixel regions are adjusted.

In addition, the present disclosure provides an endoscopic image processing method. The endoscopic image processing method includes the following steps: sensing a plurality of test lights after a plurality of ambient lights are irradiated on an object and then are reflected by the object to form the plurality of test lights; sensing parts of a plurality of colored light beams of the plurality of test lights that fall within a same one of a plurality of imaging ranges to generate each of a plurality of initial images, so as to generate the plurality of initial images respectively within the plurality of imaging ranges; aligning the plurality of initial images with each other to form a superimposed image; analyzing a plurality of features of the superimposed image to convert the superimposed image into a feature image; reading and identifying colors of a plurality of pixel points in a plurality of pixel regions of the feature image; comparing color depths of the plurality of pixel points in each of the plurality of pixel regions of the feature image with each other; determining a largest one of the color depths of the plurality of pixel points that are classified in a same one of a plurality of color tones in each of the plurality of pixel regions, as a maximum color depth of the same one of the plurality of color tones in each of the plurality of pixel regions of the feature image; analyzing a relationship between the color depth of each of the plurality of pixel points and the maximum color depth that are classified in the same one of the plurality of color tones in each of the plurality of pixel regions of the feature image; adjusting the color depth of each of the plurality of pixel points according to the relationship between the color depth of each of the plurality of pixel points and the maximum color depth that are classified in the same one of the plurality of color tones in each of the plurality of pixel regions of the feature image; and generating a fusion image according to the feature image on which the color depths of all of the plurality of pixel regions are adjusted.

As described above, the present disclosure provides the endoscope device, the endoscopic medical assistance system, and the endoscopic image processing method. In the present disclosure, the endoscope captures the plurality of images of the same body part inside the human body respectively under different ones of the plurality of color light beams splitted from the ambient light. In the present disclosure, the image fusion device fuses the plurality of images of the same body part inside the human body to generate the clear image that is similar to the actual scene thereof. As a result, practicability of the clear image is more effectively improved by the present disclosure for subsequent applications, for example, an accuracy of medical diagnosis applications.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 6 is a flowchart diagram of steps of fusing a plurality of images in the endoscopic medical assistance method according to the first and second embodiments of the preset disclosure;

FIG. 7 is a flowchart diagram of steps of fusing a plurality of images in an endoscopic medical assistance method according to a third embodiment of the preset disclosure;

DETAILED DESCRIPTION OF THE EXEMPLARY EMBODIMENTS

Figure 1:
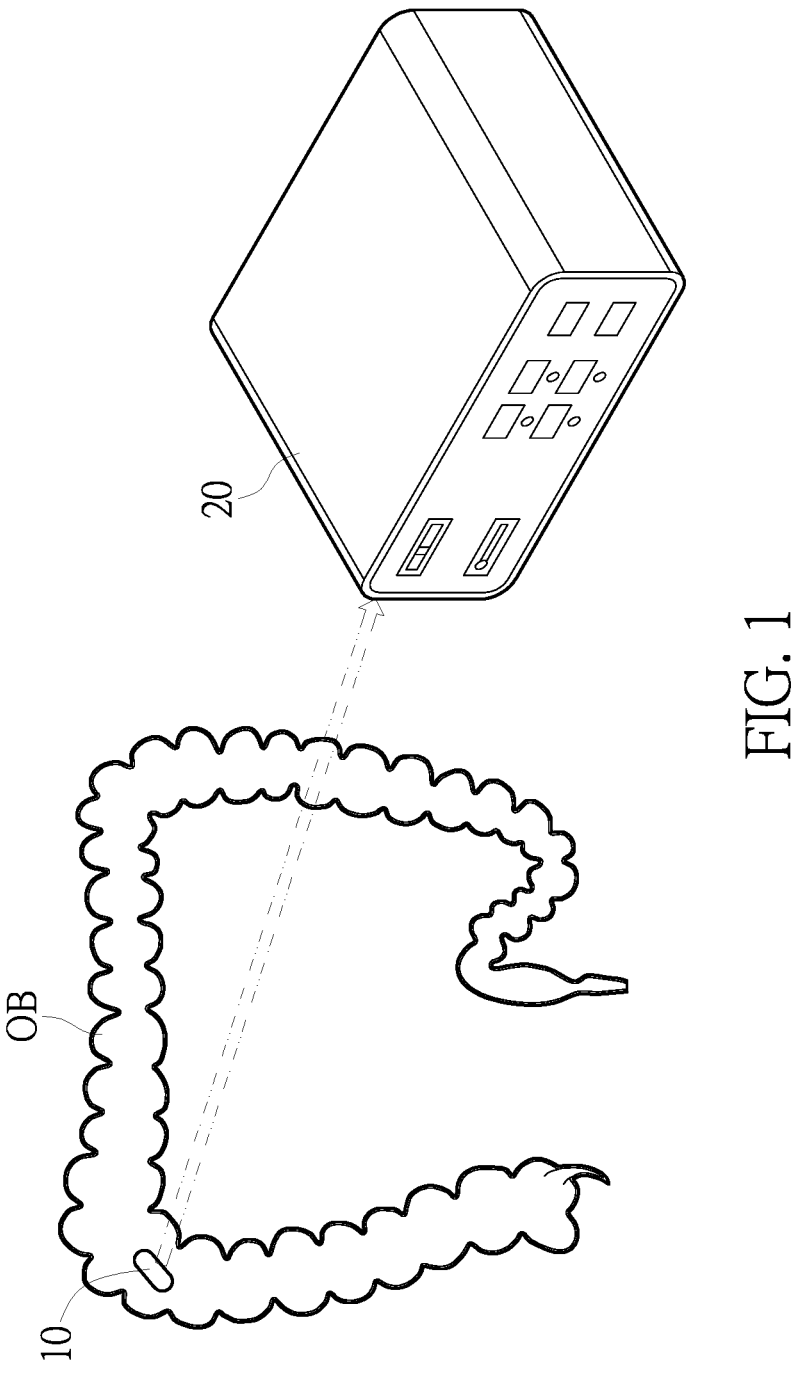
FIG. 1 is a schematic diagram of an endoscopic medical assistance system being applied to a human body according to a first embodiment of the preset disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
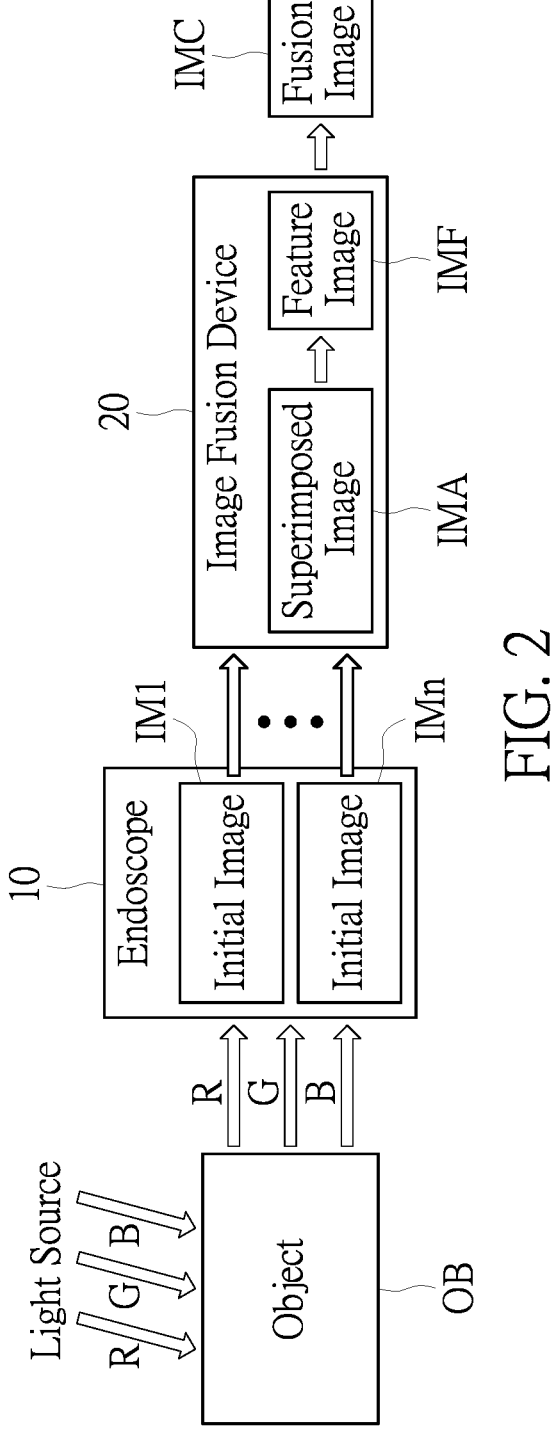
FIG. 2 is a block diagram of the endoscopic medical assistance system according to the first embodiment of the preset disclosure.
Figure 3:
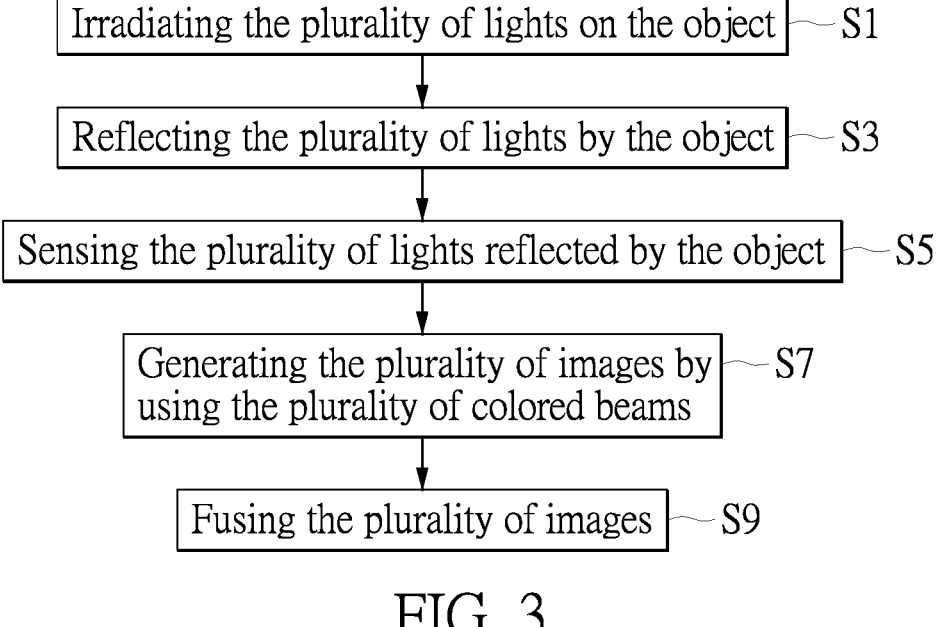
FIG. 3 is a flowchart diagram of an endoscopic medical assistance method according to the first embodiment of the preset disclosure.

Reference is made to FIGS. 1 to 3 and FIG. 6, in which FIG. 1 is a schematic diagram of an endoscopic medical assistance system being applied to a human body according to a first embodiment of the preset disclosure, FIG. 2 is a block diagram of the endoscopic medical assistance system according to the first embodiment of the preset disclosure, FIG. 3 is a flowchart diagram of an endoscopic medical assistance method according to the first embodiment of the preset disclosure, and FIG. 6 is a flowchart diagram of steps of fusing a plurality of images in the endoscopic medical assistance method according to the first and second embodiments of the preset disclosure.

The endoscopic medical assistance system of the first embodiment of the preset disclosure as shown in FIGS. 1 and 2 may perform steps S5 to S9 of the endoscopic medical assistance method as shown in FIG. 3.

As shown in FIG. 1, the endoscopic medical assistance system of the first embodiment of the preset disclosure includes an endoscope 10 and an image fusion device 20. It should be understood that, the endoscope 10 described herein may be replaced with other devices functioning to capture images.

After a plurality of lights inside an object OB such as a human body are irradiated on the object OB (in step S1 as shown in FIG. 3), the plurality of lights are reflected by the object OB to form a plurality of test lights (in step S3 as shown in FIG. 3).

When the endoscope 10 is placed into the object OB such as the human body, the endoscope 10 senses the plurality of test lights that are reflected by the object OB (in step S5 as shown in FIG. 3). The endoscope 10 senses parts of a plurality of colored light beams of the plurality of test lights that fall within a same one of a plurality of imaging ranges to generate each of a plurality of initial images IM1 to IMn, so as to generate the plurality of initial images IM1 to IMn respectively within the plurality of imaging ranges (in step S7 as shown in FIG. 3).

It is worth noting that, the endoscope 10 of the endoscopic medical assistance system of the preset disclosure captures the plurality of initial images IM1 to IMn of the object OB such as the same body part of the human body respectively under different lights (that have different colors). For example, the endoscope 10 captures the plurality of initial images IM1 to IMn inside a gastrointestinal tract of the human body as shown in FIG. 1. Therefore, colors, solution and other features of the plurality of initial images IM1 to IMn captured by the endoscope 10 are different from each other.

The plurality of lights irradiated on the object OB such as the human body may include a plurality of ambient lights inside the object OB (or light emitted by an additional light source disposed on the endoscope 10). For example, the lights irradiated on the object OB may include a white light formed from a red light R mixed with a green light G and a blue light B as shown in FIG. 2, but the present disclosure is not limited thereto.

For example, in the endoscopic medical assistance system of the preset disclosure, the endoscope 10 may capture the plurality of initial images IM1 to IMn of the object OB such as the human body under infrared light and X-ray radiation, and then the image fusion device 20 may further fuse the plurality of initial images IM1 to IMn to generate a fusion image.

After the plurality of initial images IM1 to IMn of the object OB are captured by the endoscope 10, the endoscope 10 is wirely or wirelessly connected to the image fusion device 20 and outputs the plurality of initial images IM1 to IMn to the image fusion device 20. The image fusion device 20 fuses the plurality of initial images IM1 to IMn of the same scene (such as the same body part of the human body) to generate the clear fusion image that is similar to the actual scene (in step S9 as shown in FIG. 3).

The image fusion device 20 performs processes on the plurality of initial images IM1 to IMn captured by the endoscope 10 to fuse the plurality of initial images IM1 to IMn (in steps S91, S93 and S101 to S115 as shown in FIG. 6), as described in detail in the following.

As shown in FIG. 2, in the first embodiment, the image fusion device 20 of the endoscopic medical assistance system of the preset disclosure obtains the plurality of initial images IM1 to IMn from the endoscope 10, and then aligns the plurality of initial images IM1 to IMn with each other to form the superimposed image IMA (in step S91 as shown in FIG. 6).

As shown in FIG. 2, the image fusion device 20 analyzes a plurality of features of the superimposed image IMA and accordingly converts the superimposed image IMA into a feature image IMF as shown in FIG. 2 (in step S93 as shown in FIG. 6).

The image fusion device 20 reads and identifies colors of a plurality of pixel points in a plurality of pixel regions of the feature image IMF (in step S101 as shown in FIG. 6).

The image fusion device 20 compares color depths of the pixel points that are classified in a same one of a plurality of color tones in each of the plurality of pixel regions of the feature image IMF with each other (in step S103 as shown in FIG. 6). The image fusion device 20 determines a largest one of the color depths of the pixel points that are classified in the same one of the plurality of color tones in each of the plurality of pixel regions of the feature image IMF, as a maximum color depth of the same one of the plurality of color tones (in step S105 as shown in FIG. 6) of each of the plurality of pixel regions of the feature image IMF.

It should be understood that, the size and the number of the plurality of initial images IM1 to IMn captured by the endoscope 10, the size and the number of the plurality of initial images IM1 to IMn that are aligned with each other by the image fusion device 20, and the area and the number of the plurality of pixel regions divided from the feature image IMF, may be determined according to actual requirements, but the present disclosure is not limited thereto.

The image fusion device 20 may determine the maximum color depths respectively of the plurality of color tones in each of the plurality of pixel regions of the feature image IMF, such as, but not limited to the maximum color depth of a red tone, the maximum color depth of a blue tone and the maximum color depth of a green tone.

The image fusion device 20 analyzes a relationship between the color depth of each of the plurality of pixel points and the maximum color depth that are classified in the same one of the plurality of color tones in each of the plurality of pixel regions of the feature image IMF (in step S107 as shown in FIG. 6).

The image fusion device 20 determines whether or not the relationship between the color depth of each of the plurality of pixel points and the maximum color depth that are classified in the same one of the plurality of color tones in each of the plurality of pixel regions of the feature image IMF meets a preset relationship (in step S109 as shown in FIG. 6) to determine whether or not to adjust the color depth of each of the plurality of pixel points of the feature image IMF.

When the image fusion device 20 determines that the relationship between the color depth of any one of the plurality of pixel points and the maximum color depth that are classified in the same one of the plurality of color tones in any one of the plurality of pixel regions of the feature image IMF meets the preset relationship, the image fusion device 20 does not adjust the color depth of the one of the plurality of pixel points. If the image fusion device 20 determines that others of the plurality of pixel regions of the feature image IMF are not processed (in step S113 as shown in FIG. 6), the image fusion device 20 performs the same processes on the others of the plurality of pixel regions of the feature image IMF as that of the one of the plurality of pixel points.

Conversely, the image fusion device 20 may determine that the relationship between the color depth of any one of the plurality of pixel points and the maximum color depth that are classified in the same one of the plurality of color tones in any one of the plurality of pixel regions of the feature image IMF does not meet the preset relationship. Under this condition, the image fusion device 20 adjusts the color depth of the one of the plurality of pixel points, according to the maximum color depth that is classified in the same one of the plurality of color tones with the color depth of the one of the plurality of pixel points in the same one of the plurality of pixel regions of the feature image IMF (in step S111 as shown in FIG. 6). For example, the image fusion device 20 fuses the color depth of the one of the plurality of pixel points with the maximum color depth that is classified in the same one of the plurality of color tones with the color depth of the one of the plurality of pixel points in the same one of the plurality of pixel regions of the feature image IMF.

For example, the image fusion device 20 may determine that a color difference between the color depth of any one of the plurality of pixel points and the maximum color depth that are classified in the same one of the plurality of color tones in the same one of the plurality of pixel regions of the feature image IMF is larger than a color difference threshold (that is the preset relationship as described above). Under this condition, the image fusion device 20 adjusts the color depth of the one of the plurality of pixel points, according to the maximum color depth that is classified in the same one of the plurality of color tones with the color depth of the one of the plurality of pixel points in the same one of the plurality of pixel regions of the feature image IMF.

After all of the plurality of pixel points in the plurality of pixel regions of the feature image IMF are processed (in step S113 as shown in FIG. 6), the image fusion device 20 generates the fusion image IMC as shown in FIG. 2 according to the adjusted/fused feature image IMF (in step S115 as shown in FIG. 6).

Figure 4:
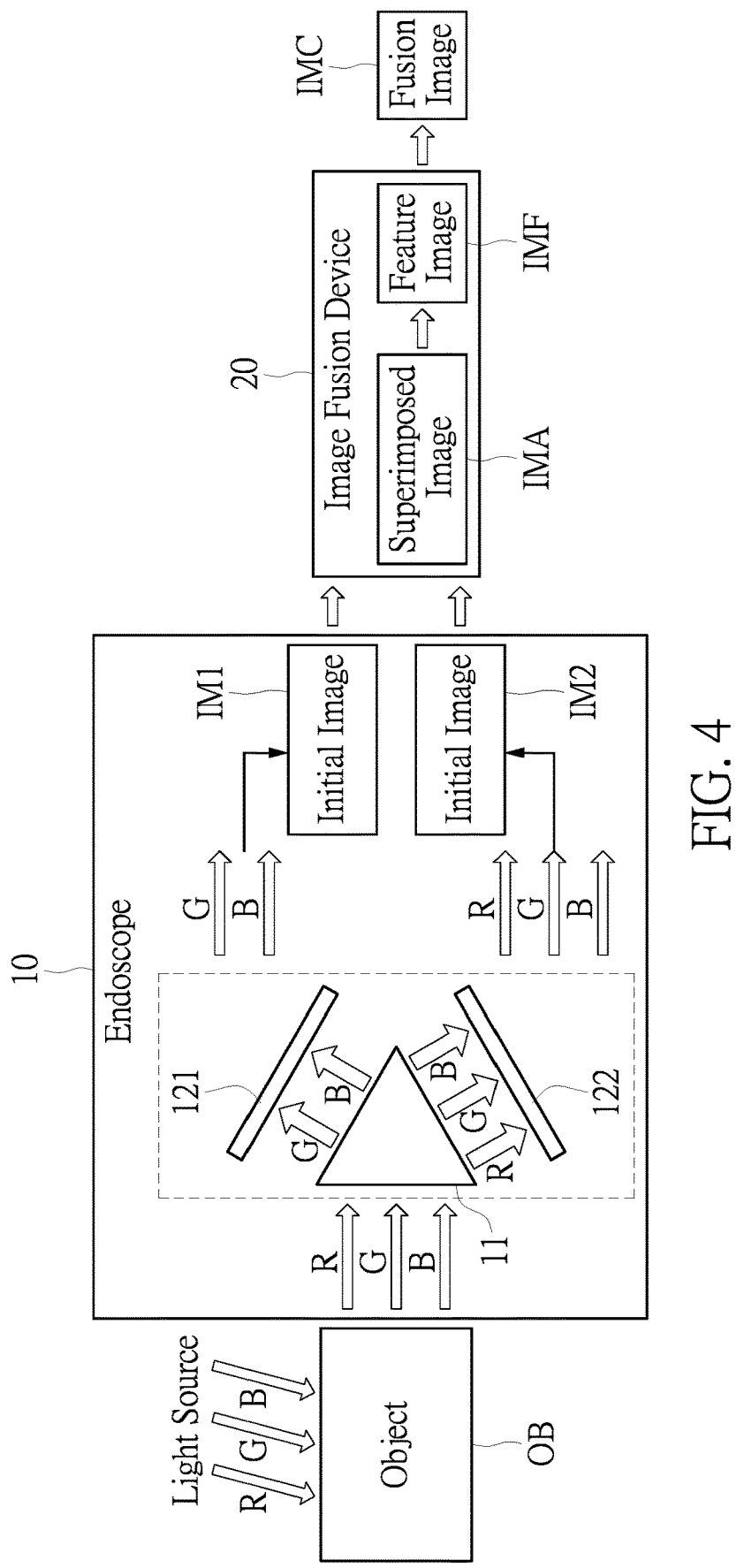
FIG. 4 is a block diagram of an endoscopic medical assistance system according to a second embodiment of the preset disclosure.
Figure 5:
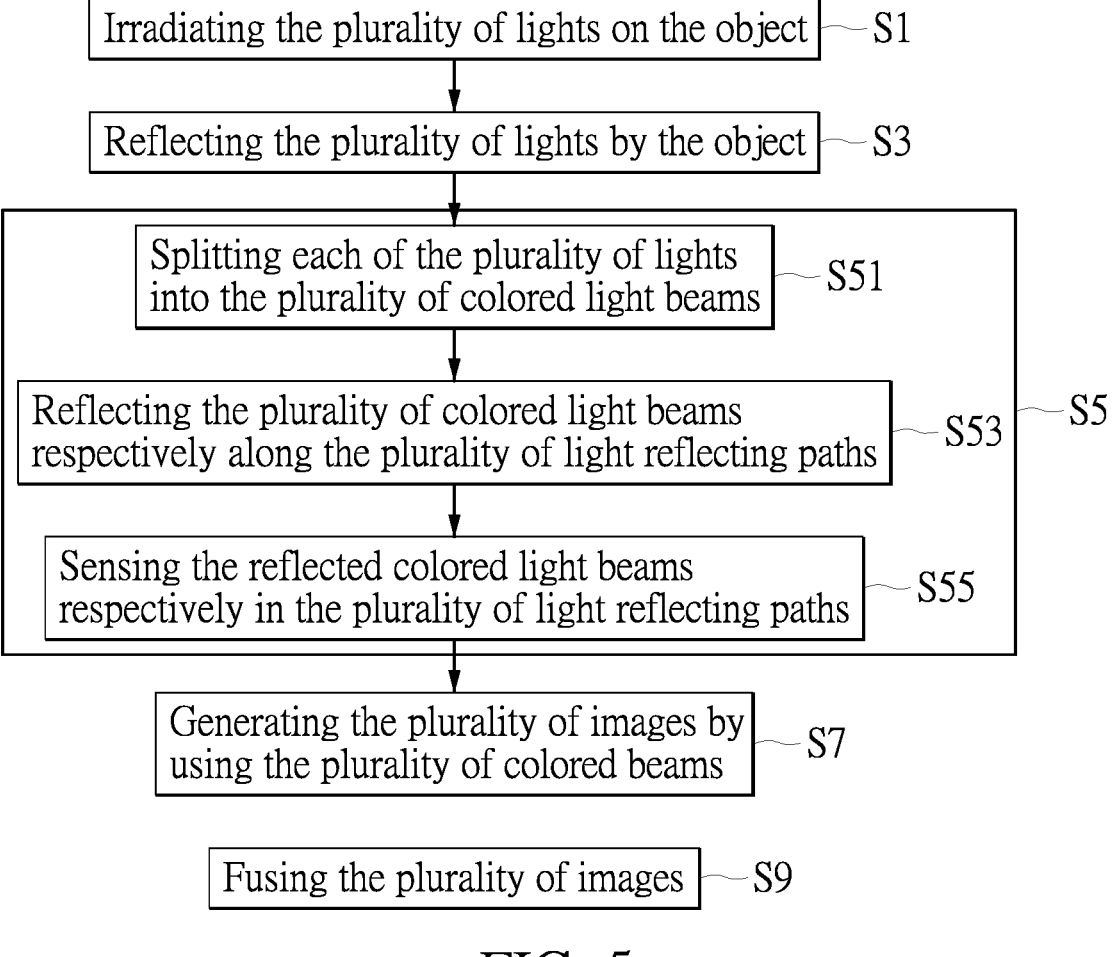
FIG. 5 is a flowchart diagram of an endoscopic medical assistance method according to the second embodiment of the preset disclosure.

Reference is made to FIGS. 4 and 6, in which FIG. 4 is a block diagram of an endoscopic medical assistance system according to a second embodiment of the preset disclosure, and FIG. 5 is a flowchart diagram of an endoscopic medical assistance method according to the second embodiment of the preset disclosure.

As shown in FIG. 4, the endoscopic medical assistance system of the second embodiment of the preset disclosure includes the endoscope 10 and the image fusion device 20.

For example, in the second embodiment, the endoscope 10 of the endoscopic medical assistance system of the preset disclosure includes a beam splitter (such as a prism 1 as shown in FIG. 4), and a plurality of image sensors 121 and 122 as shown in FIG. 4 (such as CMOS image sensors), but the present disclosure is not limited thereto. In practice, the number of the beam splitters and the image sensors that are included in the endoscopic medical assistance system of the preset disclosure may be determined according to actual requirements.

After the plurality of lights are irradiated inside the object OB such as the human body (in step S1 as shown in FIG. 5), the plurality of lights are reflected by the object OB to form the plurality of test lights (in step S3 as shown in FIG. 5).

It is worth noting that, the beam splitter (such as the prism 1 as shown in FIG. 4) included in the endoscope 10 of the endoscopic medical assistance system of the second embodiment of the preset disclosure may split each of the plurality of test lights into a plurality of colored light beams (in step S51 as shown in FIG. 5). The beam splitter (such as the prism 1 as shown in FIG. 4) reflects the plurality of colored light beams of the plurality of test lights respectively along a plurality of light reflecting paths (in step S53 as shown in FIG. 5).

The plurality of image sensors 121 and 122 are disposed respectively within the plurality of imaging ranges. Each of the plurality of image sensors 121 and 122 are disposed in a number of the plurality of light reflecting paths along which the plurality of colored light beams are reflected by the beam splitter (such as the prism 1 as shown in FIG. 4). The plurality of image sensors 121 and 122 sense the plurality of colored light beams in the plurality of light reflecting paths respectively within the plurality of imaging ranges (in step S55 as shown in FIG. 5) to respectively generate the plurality of initial images (in step S7 as shown in FIG. 5).

For example, as shown in FIG. 4, the image sensor 121 senses a green light beam and a blue light beam to generate an initial image IM1, and the image sensor 122 senses a red light beam, a green light beam and a blue light beam to generate an initial image IM2.

The image fusion device 20 of the endoscopic medical assistance system of the second embodiment of the preset disclosure fuses the initial image IM1 from the image sensor 121 with the initial image IM2 from the image sensor 122 to generate a clear image (in steps S91, S93 and S101 to S115 as described above).

Reference is made to FIG. 7, which is a flowchart diagram of steps of fusing a plurality of images in an endoscopic medical assistance method according to a third embodiment of the preset disclosure. The same descriptions of the third and first embodiments of the preset disclosure are not repeated herein.

Differences between the third and first embodiments of the preset disclosure are described in the following. In the third embodiment, the image fusion device (such as the image fusion device 20 described above) may, according to difference relationships between the color depths of the plurality of pixel points and the maximum color depths that respectively are classified in the plurality of color tones in each of the plurality of pixel regions of the feature image (such as the feature image IMF described above), set a plurality of weight values (in step S205 as shown in FIG. 7).

If necessary, the image fusion device may establish a weight chart of the feature image according to the plurality of weight values respectively of the plurality of pixel points of the feature image (in step S207 as shown in FIG. 7).

The image fusion device may determine adjustment degrees of the color depths of the plurality of pixel points of the feature image according to the plurality of weight values respectively of the plurality of pixel points (on the weight chart) (in step S209 as shown in FIG. 7).

After the image fusion device adjusts the color depths of some of the plurality of pixel points of the feature image respectively according to the plurality of weight values of the plurality of pixel points (on the weight chart), the image fusion device generates the fusion image according to the adjusted feature image (in step S115 as shown in FIG. 7).

Figure 8:
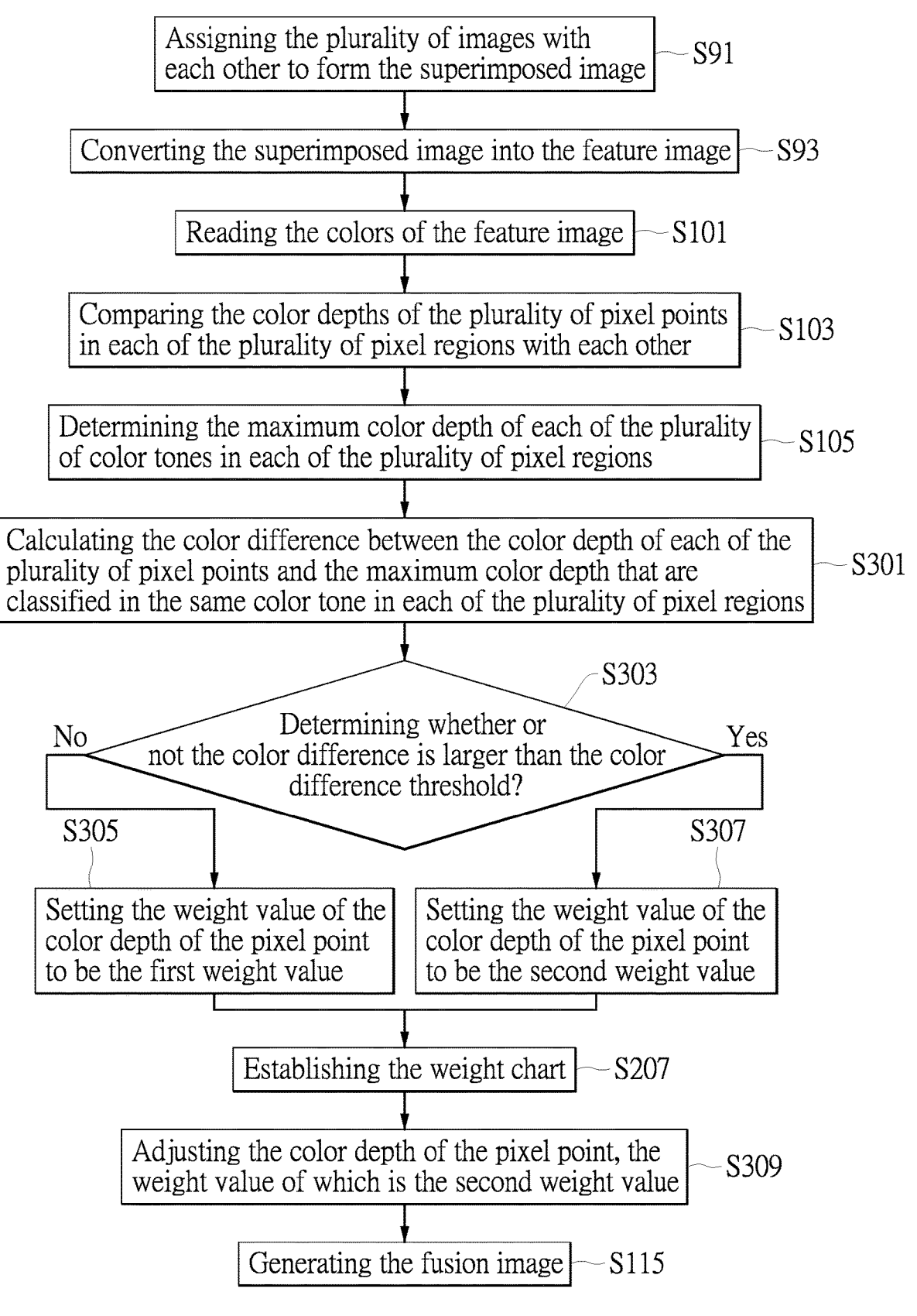
FIG. 8 is a flowchart diagram of steps of fusing a plurality of images in an endoscopic medical assistance method according to a fourth embodiment of the preset disclosure.

Reference is made to FIG. 8, which is a flowchart diagram of steps of fusing a plurality of images in an endoscopic medical assistance method according to a fourth embodiment of the preset disclosure.

In the fourth embodiment, the image fusion device (such as the image fusion device 20 described above) of the endoscopic medical assistance system calculates the color difference between the color depth of each of the plurality of pixel points and the maximum color depth that are classified in the same one of the plurality of color tones in the same one of the plurality of pixel regions of the feature image (such as the feature image IMF described above) (in step S301 as shown in FIG. 8).

The image fusion device determines whether or not the color difference between the color depth of each of the plurality of pixel points and the maximum color depth that are classified in the same one of the plurality of color tones in the same one of the plurality of pixel regions of the feature image is larger than the color difference threshold (in step S303 as shown in FIG. 8).

If the image fusion device determines that the color difference between the color depth of any one of the plurality of pixel points and the maximum color depth that are classified in the same one of the plurality of color tones in each of the plurality of pixel regions of the feature image is not larger than the color difference threshold, the image fusion device sets the weight value of the one of the plurality of pixel points to be a first weight value such as, but not limited to "1" (in step S305 as shown in FIG. 8).

Conversely, if the image fusion device determines that the color difference between the color depth of each of the plurality of pixel points and the maximum color depth that are classified in the same one of the plurality of color tones in the same one of the plurality of pixel regions of the feature image is larger than the color difference threshold, the image fusion device sets the weight value of the one of the plurality of pixel points to be a second weight value such as, but not limited to "0" (in step S307 as shown in FIG. 8).

If necessary, the image fusion device may establish the weight chart of the feature image according to the plurality of weight values respectively of the plurality of pixel points of the feature image (in step S207 as shown in FIG. 8).

If the weight value of the color depth of any one of the plurality of pixel points is equal to the second weight value (on the weight chart), the image fusion device adjusts the color depth of the one of the plurality of pixel points according to the maximum color depth that is classified in the same one of the plurality of color tones with the color depth of the one of the plurality of pixel points in the same one of the plurality of pixel regions of the feature image (in step S309 as shown in FIG. 8). However, if the weight value of the color depth of any one of the plurality of pixel points is equal to the first weight value (on the weight chart), the image fusion device does not adjust the color depth of the one of the plurality of pixel points. Finally, the image fusion device generates the fusion image according to the adjusted feature image (in step S115 as shown in FIG. 8).

Figure 9:
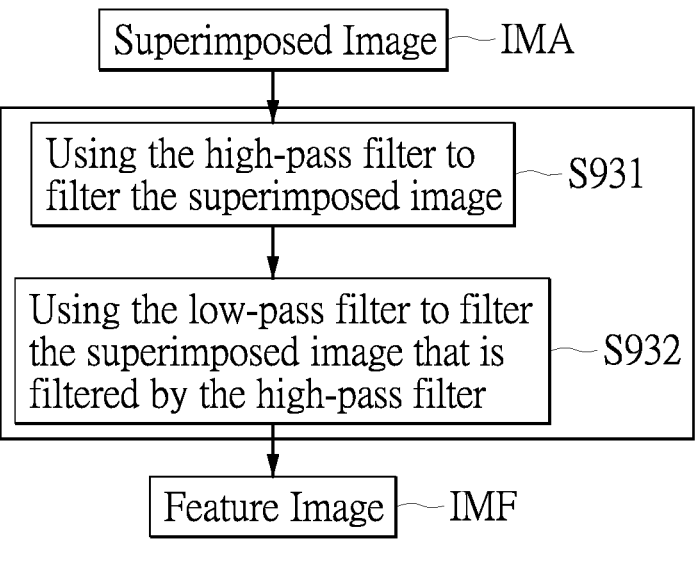
FIG. 9 is a flowchart diagram of steps of fusing a plurality of images in an endoscopic medical assistance method according to a fifth embodiment of the preset disclosure.

Reference is made to FIG. 9, which is a flowchart diagram of steps of fusing a plurality of images in an endoscopic medical assistance method according to a fifth embodiment of the preset disclosure.

In the fifth embodiment, when the image fusion device of the endoscopic medical assistance system of the preset disclosure obtains an input image (that is the superimposed image IMA described above), the image fusion device removes a background color from the input image to generate a foreground image as a subsequent comparison image (that is the feature image IMF described above).

For example, the image fusion device may include a high-pass filter and a low-pass filter. The high-pass filter filters the superimposed image IMA (in step S931 as shown in FIG. 9). Then, the low-pass filter filters the superimposed image IMA that is filtered by the high-pass filter to generate the feature image IMF (in step S932 as shown in FIG. 9).

Figure 10:
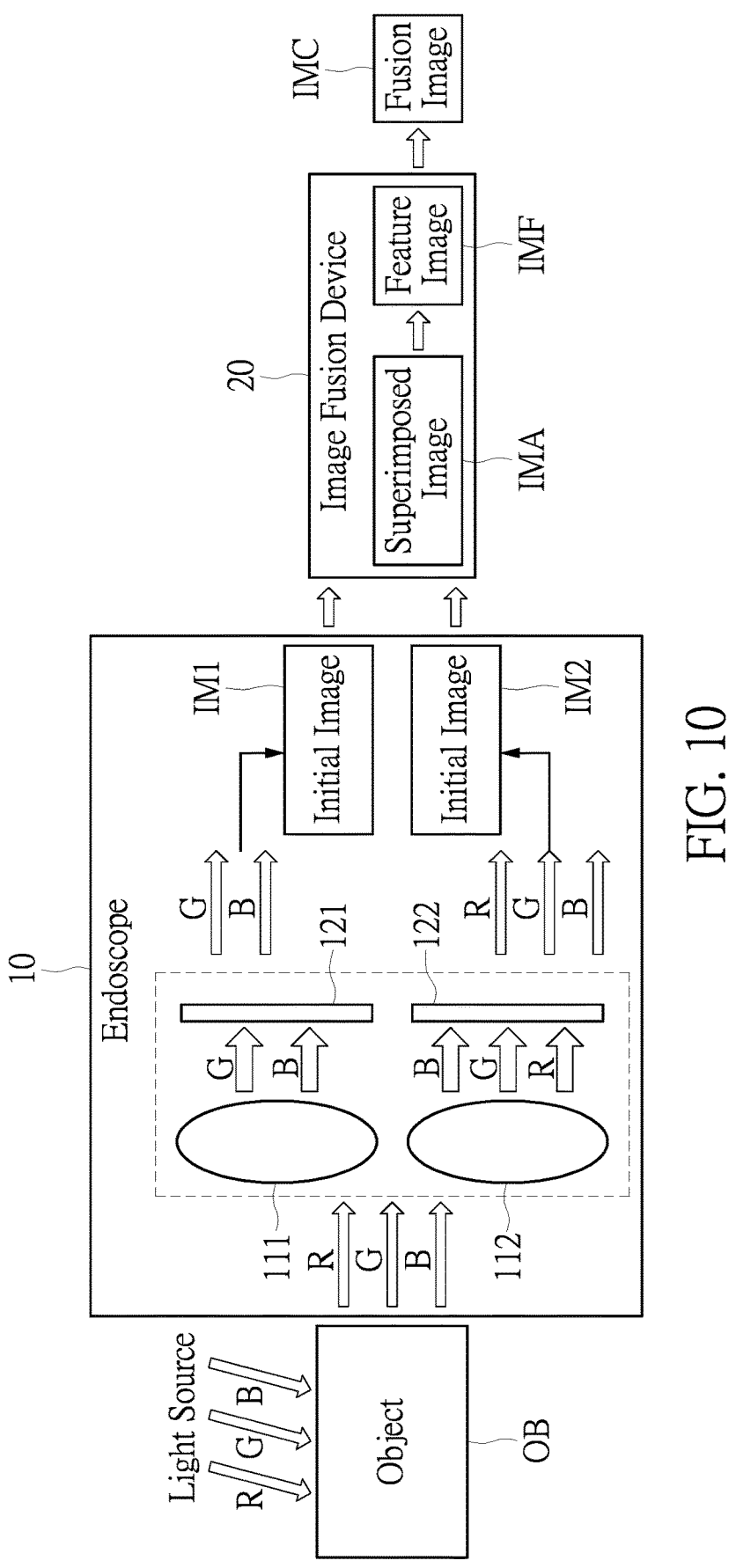
FIG. 10 is a block diagram of an endoscopic medical assistance system according to a sixth embodiment of the preset disclosure.

Reference is made to FIG. 10, which is a block diagram of an endoscopic medical assistance system according to a sixth embodiment of the preset disclosure.

The endoscopic medical assistance system of the sixth embodiment of the preset disclosure includes the endoscope 10 and the image fusion device 20.

As described above, in the second embodiment, the endoscope 10 of the endoscopic medical assistance system of the preset disclosure only includes only one beam splitter (such as the prism 1 as shown in FIG. 4). In practice, the endoscope 10 of the endoscopic medical assistance system of the preset disclosure may include more than one beam splitters.

For example, as shown in FIG. 10, in the sixth embodiment, the endoscope 10 of the endoscopic medical assistance system of the preset disclosure includes a first beam splitter (such as a biconvex lens 111 as shown in FIG. 10), a second beam splitter (such as a biconvex lens 112 as shown in FIG. 10) and the plurality of image sensors 121 and 122 (such as the CMOS image sensors), but the present disclosure is not limited thereto.

After the plurality of lights are irradiated inside the object OB such as the human body, the plurality of lights are reflected by the object OB to form the plurality of test lights such as a red light R, a green light G and a blue light B.

The image sensor 121 only senses the test lights passing through the first beam splitter (such as the biconvex lens 111 as shown in FIG. 10), such as only the green light G and the blue light B, to generate the initial image IM1 as shown in FIG. 10.

In addition, the image sensor 121 senses the test lights passing through the second beam splitter (such as the biconvex lens 112 as shown in FIG. 10), such as the red light R, the green light G and the blue light B, to generate the initial image IM2.

The image fusion device 20 fuses the initial image IM1 with the initial image IM2 to generate the fusion image as described in the second embodiment. Therefore, the same descriptions of the second and the sixth embodiments are not repeated herein.

In conclusion, the present disclosure provides the endoscope device, the endoscopic medical assistance system, and the endoscopic image processing method. In the present disclosure, the endoscope captures the plurality of images of the same body part inside the human body respectively under different ones of the plurality of color light beams splitted from the ambient light. In the present disclosure, the image fusion device fuses the plurality of images of the same body part inside the human body to generate the clear image that is similar to the actual scene thereof. As a result, practicability of the clear image is more effectively improved by the present disclosure for subsequent applications, for example, an accuracy of medical diagnosis applications.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An endoscopic medical assistance system, comprising:
an endoscope, wherein, after a plurality of ambient lights are irradiated on an object and then are reflected by the object to form a plurality of test lights, the endoscope senses parts of a plurality of colored light beams of the plurality of test lights that fall within a same one of a plurality of imaging ranges to generate each of a plurality of initial images, so as to generate the plurality of initial images within the plurality of imaging ranges, respectively; and an image fusion device connected to the endoscope, wherein the image fusion device aligns the plurality of initial images with each other to form a superimposed image, the image fusion device analyzes a plurality of features of the superimposed image and accordingly converts the superimposed image into a feature image, the image fusion device reads and identifies colors of a plurality of pixel points in a plurality of pixel regions of the feature image, the image fusion device compares color depths of the plurality of pixel points in each of the plurality of pixel regions of the feature image with each other, the image fusion device determines a largest one of the color depths of the plurality of pixel points that are classified in a same one of a plurality of color tones in each of the plurality of pixel regions as a maximum color depth of the same one of the plurality of color tones in each of the plurality of pixel regions of the feature image, the image fusion device analyzes a relationship between the color depth of each of the plurality of pixel points and the maximum color depth that are classified in the same one of the plurality of color tones in each of the plurality of pixel regions of the feature image, the image fusion device adjusts the color depth of each of the plurality of pixel points of the feature image according to the relationship between the color depth of each of the plurality of pixel points and the maximum color depth that are classified in the same one of the plurality of color tones in each of the plurality of pixel regions of the feature image, and the image fusion device generates a fusion image according to the feature image on which the color depths of all of the plurality of pixel regions are adjusted.

2. The endoscopic medical assistance system according to claim 1, wherein the endoscope includes:

a beam splitter configured to split each of the plurality of test lights into a number of the plurality of colored light beams, and to reflect the plurality of colored light beams of the plurality of test lights respectively along a plurality of light reflecting paths; and a plurality of image sensors disposed respectively within the plurality of imaging ranges, wherein each of the plurality of image sensors are disposed in a number of the plurality of light reflecting paths;

wherein the plurality of image sensors sense the plurality of colored light beams in the plurality of light reflecting paths to generate the plurality of initial images within the plurality of imaging ranges, respectively.

3. The endoscopic medical assistance system according to claim 2, wherein the plurality of colored light beams sensed by one of the plurality of image sensors are a green light beam and a blue light beam, and the plurality of colored light beams sensed by another one of the plurality of image sensors are a red light beam, a green light beam and a blue light beam.

4. The endoscopic medical assistance system according to claim 1, wherein, when the relationship between the color depth of any one of the plurality of pixel points and the maximum color depth that are classified in the same one of the plurality of color tones in a same one of the plurality of pixel regions of the feature image does not meet a preset relationship, the image fusion device adjusts the color depth of the one of the plurality of pixel points according to the maximum color depth, and the image fusion device generates the fusion image according to the feature image on which the color depths of all of the plurality of pixel regions are adjusted according to the maximum color depths of the plurality of pixel regions.

5. The endoscopic medical assistance system according to claim 1, wherein, when a color difference between the color depth of any one of the plurality of pixel points and the maximum color depth that are classified in the same one of the plurality of color tones in a same one of the plurality of pixel regions of the feature image is larger than a color difference threshold, the image fusion device adjusts the color depth of the one of the plurality of pixel points according to the maximum color depth.

6. The endoscopic medical assistance system according to claim 1, wherein the image fusion device sets a plurality of weight values according to the relationships between the color depths of the plurality of pixel points and the maximum color depths that are classified in the plurality of color tones in each of the plurality of pixel regions of the feature image, and the image fusion device determines adjustment degrees of the color depths of the plurality of pixel points of the feature image according to the plurality of weight values of the plurality of pixel points of the feature image, respectively.

7. The endoscopic medical assistance system according to claim 6, wherein the image fusion device establishes a weight chart of the feature image according to the plurality of weight values of the plurality of pixel points of the feature image, and the image fusion device determines the adjustment degrees of the color depths of the plurality of pixel points of the feature image according to the plurality of weight values on the weight chart.

8. An endoscopic image processing method, comprising the following steps:

sensing a plurality of test lights after a plurality of ambient lights are irradiated on an object and then are reflected by the object to form the plurality of test lights;

sensing parts of a plurality of colored light beams of the plurality of test lights that fall within a same one of a plurality of imaging ranges to generate each of a plurality of initial images, so as to generate the plurality of initial images respectively within the plurality of imaging ranges;

aligning the plurality of initial images with each other to form a superimposed image;

analyzing a plurality of features of the superimposed image to convert the superimposed image into a feature image;

reading and identifying colors of a plurality of pixel points in a plurality of pixel regions of the feature image;

comparing color depths of the plurality of pixel points in each of the plurality of pixel regions of the feature image with each other;

determining a largest one of the color depths of the plurality of pixel points that are classified in a same one of a plurality of color tones in each of the plurality of pixel regions, as a maximum color depth of the same one of the plurality of color tones in each of the plurality of pixel regions of the feature image;

analyzing a relationship between the color depth of each of the plurality of pixel points and the maximum color depth that are classified in the same one of the plurality of color tones in each of the plurality of pixel regions of the feature image;

adjusting the color depth of each of the plurality of pixel points according to the relationship between the color depth of each of the plurality of pixel points and the maximum color depth that are classified in the same one of the plurality of color tones in each of the plurality of pixel regions of the feature image; and generating a fusion image according to the feature image on which the color depths of all of the plurality of pixel regions are adjusted.

\* \* \* \* \*